United States Patent [19]

Yokomichi et al.

[11] 4,399,143

[45] Aug. 16, 1983

[54] PHENOXYBUTYLTRIAZOLE COMPOUND, AGRICULTURAL AND HORTICULTURAL FUNGICIDAL COMPOSITION CONTAINING THE SAME, AND PROCESS FOR PRODUCING THE SAME

[75] Inventors: Isao Yokomichi, Moriyama; Takahiro Haga, Kusatsu; Terumasa Komyoji, Moriyama; Toshio Nakajima, Kusatsu; Norifusa Matsuo, Moriyama, all of Japan

[73] Assignee: Ishihara Sangyo Kaisha, Ltd., Osaka, Japan

[21] Appl. No.: 305,676

[22] Filed: Sep. 25, 1981

[30] Foreign Application Priority Data

Sep. 25, 1980 [JP] Japan .................. 55-133538

[51] Int. Cl.$^3$ .............. A01N 43/64; C07D 401/12; C07D 401/14; C07D 249/08
[52] U.S. Cl. .................. 424/263; 424/269; 546/276; 546/256; 548/262
[58] Field of Search ............. 546/276, 256; 548/262; 424/263, 269

[56] References Cited

U.S. PATENT DOCUMENTS

| | | | |
|---|---|---|---|
| 3,912,752 | 10/1975 | Meiser et al. | 548/262 |
| 4,048,318 | 9/1977 | Meiser et al. | 548/262 |
| 4,147,791 | 4/1979 | Meiser et al. | 548/262 |
| 4,154,842 | 5/1979 | Kramer et al. | 424/273 R |
| 4,215,127 | 7/1980 | Rogers et al. | 424/269 |
| 4,229,459 | 10/1980 | Kramer et al. | 424/245 |
| 4,255,434 | 3/1981 | Kramer et al. | 548/262 |

*Primary Examiner*—Norma S. Milestone
*Attorney, Agent, or Firm*—Sughrue, Mion, Zinn, Macpeak & Seas

[57] ABSTRACT

A phenoxybutyltriazole compound represented by the following formula (I):

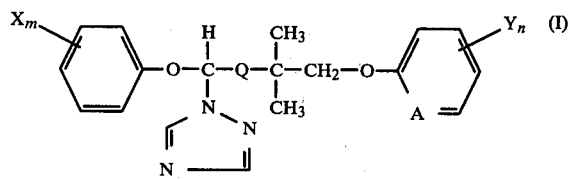

wherein X is a halogen atom, a phenyl group or a 5-trifluoromethylpyridine-2-yloxy group; Y is a halogen atom or a trifluoromethyl group; Q is a >C=O group or a >CH—OH group; A is a >CH— group or a nitrogen atom; and m and n are each an integer of 0 to 2, or a salt thereof, which is useful as an active ingredient for agricultural and horticultural fungicides, is disclosed. A process for producing the compound of the formula (I) is also disclosed.

14 Claims, No Drawings

PHENOXYBUTYLTRIAZOLE COMPOUND, AGRICULATURAL AND HORTICULTURAL FUNGICIDAL COMPOSITION CONTAINING THE SAME, AND PROCESS FOR PRODUCING THE SAME

FIELD OF THE INVENTION

The present invention relates to a novel phenoxybutyltriazole compound, an agricultural and horticultural fungicidal composition containing the same, and a process for the production of the phenoxybutyltriazole compound.

BACKGROUND OF THE INVENTION

It has been known that certain phenoxybutyltriazole compounds in the prior art, for example, those disclosed in U.S. Pat. Nos. 3,912,752, 4,048,318 and 4,147,791, have effects against fungus. However, it has not yet been known that phenoxybutyltriazole compounds having specific substituents at the 4-position of the butyl group according to the present invention have activities for controlling noxious fungus.

SUMMARY OF THE INVENTION

An object of the present invention is to provide novel phenoxybutyltriazole compounds which are effective for controlling noxious fungus.

Another object of the present invention is to provide compositions which have fungicidal activities.

A further object of the present invention is to provide a process for producing the novel phenoxybutyltriazole compounds.

The foregoing objects of the present invention have been attained by providing a phenoxybutyltriazole compound represented by the formula (I):

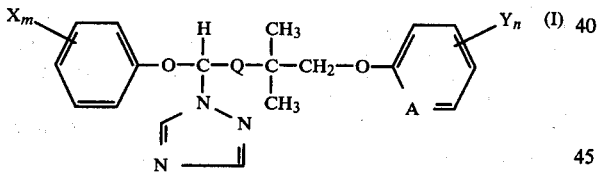

wherein X is a halogen atom, a phenyl group or a 5-trifluoromethylpyridine-2-yloxy group; Y is a halogen atom or a trifluoromethyl group; Q is a >C=O group or a >CH—OH group; A is a >CH— group or a nitrogen atom; and m and n are each an integer of 0 to 2, or salts thereof.

DETAILED DESCRIPTION OF THE INVENTION

The phenoxybutyltriazole compounds of the present invention can be those having the formula (I) wherein the halogen atom for substituents X and Y can be F, Cl, Br or I. Their salts can be acid addition salts wherein the acid can be an inorganic acid such as hydrochloric acid, sulfuric acid, nitric acid and phosphoric acid, or an organic acid such as acetic acid and p-toluenesulfonic acid.

Preferred compounds included in the phenoxybutyltriazole compounds having the formula (I) are compounds or their salts having the following formula (II) or (III):

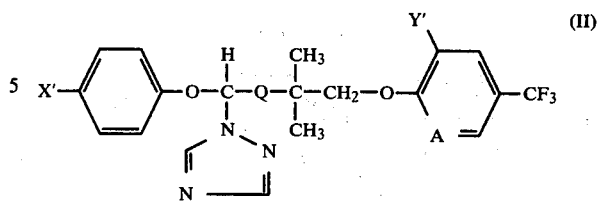

wherein X' is a halogen atom or a phenyl group; Y' is a hydrogen atom or a halogen atom; and Q and A are the same as defined above.

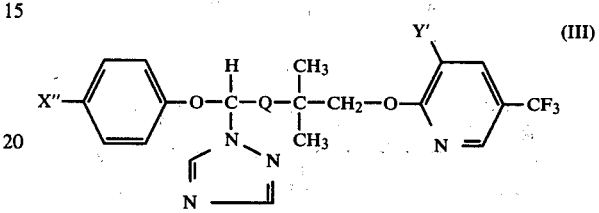

wherein X" is a halogen atom; and Y' and Q are the same as defined above.

The phenoxybutyltriazole compounds of the present invention can be produced by the following processes.

Reaction (I)

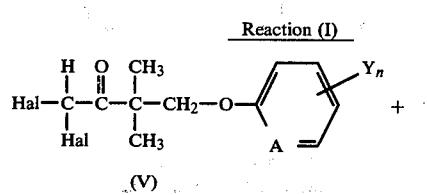

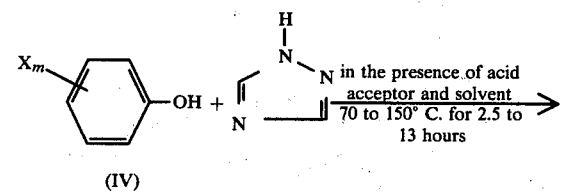

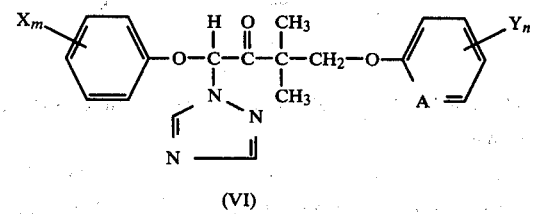

wherein Hal is a halogen atom, and X, Y, A, m and n are the same as defined above.

Examples of the acid acceptor which can be used are alkali metal salts such as potassium carbonate or potassium hydroxide, alkali metal hydrides such as sodium hydride, and alkali metal amides. Examples of the solvent which can be used are nitriles such as acetonitrile, sulfoxides such as dimethyl sulfoxide, formamides such as dimethylformamide, phosphamides such as hexamethyl phosphoric amide, ketones such as acetone or methyl ethyl ketone, ethers, and halogenated hydrocarbons.

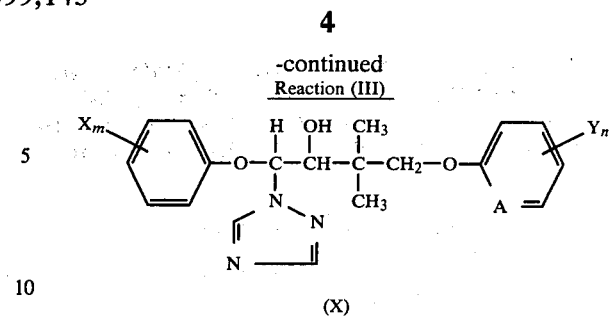

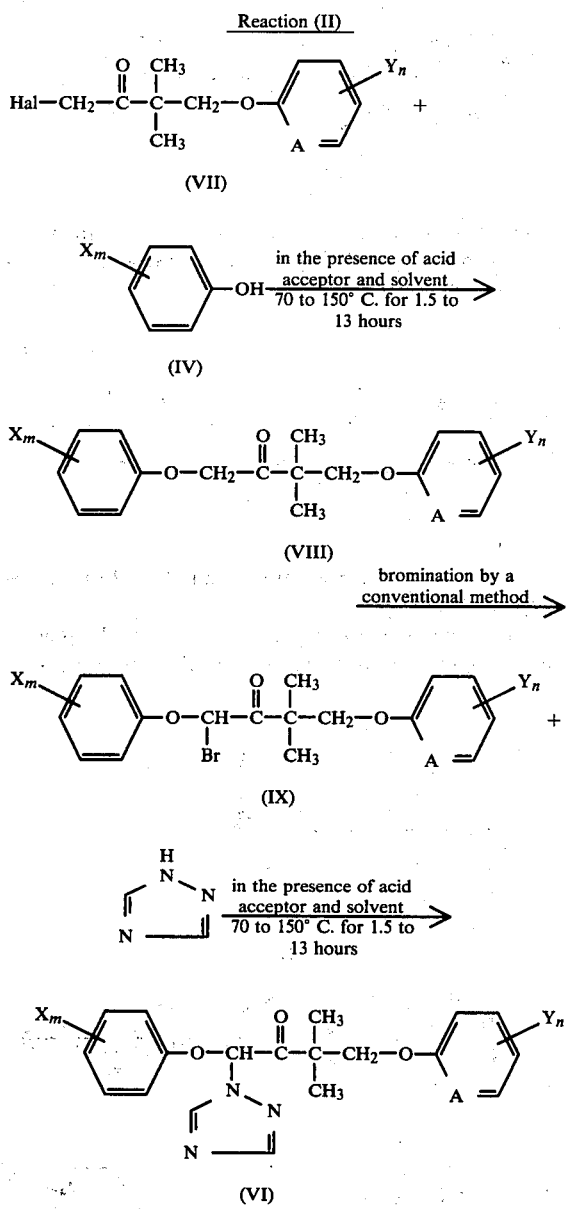

wherein X, Y, A, Hal, m and n are the same as defined above.

The acid acceptor and solvent which can be used are respectively the same as those used in the Reaction (I).

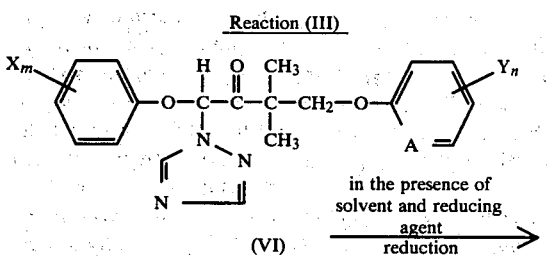

-continued

Reaction (III)

(X)

wherein X, Y, A, m and n are the same as defined above.

The Reaction (III) can be performed with a compound having a carbonyl group under the conditions used in the conventionl reduction reaction. Examples of the solvent which can be used are alcohols such as methanol, ethanol and propanol. Examples of the reducing agent which can be used are borohydrides such as sodium borohydride and sodium cyanoborohydride, and lithium aluminum hydride.

Typical examples for synthesis of the compounds of the present invention are given below.

SYNTHESIS EXAMPLE 1

3,3-Dimethyl-4-hydroxybutan-2-one (11.2 g) was dissolved in 50 ml of dimethyl sulfoxide, and nitrogen gas was passed therethrough for 20 minutes. Then, 21.6 g of 2,3-dichloro-5-trifluoromethylpyridine and 15 g of anhydrous potassium carbonate were added thereto, and the system was gradually heated to 115° C. and stirred for 4 hours at that temperature. After completion of the reaction, the product was put into ice water, extracted with methylene chloride, washed with water and dried over Glauber's salt. The solvent was distilled off to give 26.7 g of oily 3,3-dimethyl-4-(3-chloro-5trifluoromethylpyridine-2-yloxy)butan-2-one.

The oily product (29.1 g) was dissolved in 40 ml of dichloroethane, and the solution was heated to 60° C. To the solution was dropwise added a solution having 32 g of bromine dissolved in 10 ml of dichloroethane. After completion of the dropwise addition, the mixture was stirred for 20 minutes. After completion of the reaction, the product was put into ice water, neutralized with sodium hydrogencarbonate, extracted with methylene chloride, washed with water and dried over Glauber's salt. The solvent was distilled off to give 34.8 g of oily 1,1-dibromo-3,3-dimethyl-4-(3-chloro-5-trifluoromethylpyridine-2-yloxy)butan-2-one.

Nitrogen gas was passed through 6.74 g of the oily product thus-obtained for 15 minutes and mixed with 1.68 g of p-fluorophenol, 1.04 g of 1H-1,2,4-triazole, 4.14 g of potassium carbonate and 37.5 ml of methyl ethyl ketone, and the mixture was gradually heated to the reflux temperature at which it was stirred for 6 hours. After completion of the reaction, the product was allowed to stand for cooling and extracted with water-methylene chloride. The methylene chloride phase was washed with water and dried over Glauber's salt. The solvent was distilled off, and the residue was purified with a silica gel column (eluant: n-nexane/-methylene chloride) to give 5.4 g of 1-(4-fluorophenoxy)-1-(1,2,4-triazole-1-yl)-3,3-dimethyl-4-(3-chloro-5-trifluoromethylpyridine-2-yloxy)butan-2-one having a melting point of 104° to 106° C.

SYNTHESIS EXAMPLE 2

3,3-Dimethyl-4-hydroxybutan-2-one (11.2 g) was dissolved in 50 ml of dimethyl sulfoxide, and nitrogen gas was passed therethrough for 20 minutes. Then, 18.2 g of 3-trifluoromethyl-6-chloropyridine and 15 g of anhydrous potassium carbonate were added thereto, and the solution was gradually heated to 115° C. and reacted under stirring for 4 hours at that temperature. After completion of the reaction, the product was put into ice water, extracted with methylene chloride, washed with water and dried over Glauber's salt. The solvent was distilled off to give 24.8 g of oily 3,3-dimethyl-4-(5-trifluoromethylpyridine-2-yloxy)butan-2-one.

The oily product (25.8 g) was dissolved in 40 ml of dichloroethane, and the solution was heated to 60° C. To the solution was dropwise added a solution having 32 g of bromine dissolved in 10 ml of dichloroethane, and after completion of the dropwise addition, the mixture was reacted under stirring for 20 minutes. After completion of the reaction, the product was put into ice water, neutralized with sodium hydrogencarbonate, extracted with methylene chloride, washed with water and dried over Glauber's salt. The solvent was distilled off to give 35.7 g of oily 1,1-dibromo-3,3-dimethyl-4-(5-trifluoromethylpyridine-2-yloxy)butan-2-one.

Nitrogen gas was passed through 10.4 g of the oily product thus-obtained for 15 minutes and mixed with 3.2 g of p-chlorophenol, 1.73 g of 1H-1,2,4-triazole, 6.9 g of potassium carbonate and 50 ml of methyl ethyl ketone, and the mixture was gradually heated to the reflux temperature at which it was stirred for 6 hours. After completion of the reaction, the product was allowed to stand for cooling and extracted with water-methylene chloride. The methylene chloride phase was washed with water and dried over Glauber's salt. The solvent was distilled off, and the residue was purified with a silica gel column (eluant: n-hexane/methylene chloride) to give 6.53 g of 1-(4-chlorophenoxy)-1-(1,2,4-triazole-1-yl)-3,3-dimethyl-4-(5-trifluoromethylpyridine-2-yloxy)butan-2-one having a refractive index ($n_D^{20}$) of 1.5383.

SYNTHESIS EXAMPLE 3

1-(4-Chlorophenoxy)-1-(1,2,4-triazole-1-yl)-3,3-dimethyl-4-(5-trifluoromethylpyridine-2-yloxy)butan-2-one (2.27 g) obtained in Synthesis Example 2 was dissolved in 20 ml of isopropyl alcohol, and after gradually adding 208 mg of sodium borohydride, the solution was reacted under stirring for 15 hours, and further heated under reflux condition for 1 hour. After completion of the reaction, the product was allowed to stand for cooling, a suitable amount of water was added thereto, and the mixture was stirred for 3 hours at room temperature (i.e., about 20° to 30° C.). The mixture was then extracted with methylene chloride and dried over Glauber's salt. The solvent was distilled off, and the residue was purified with a silica gel column (eluant: n-hexane/methylene chloride) to give 1.97 g of 1-(4-chlorophenoxy)-1-(1,2,4-triazole-1-yl)-3,3-dimethyl-4-(5-trifluoromethylpyridine-2-yloxy)butan-2-ol having a refractive index ($n_D^{20}$) of 1.5010.

Typical compounds of the present invention are listed below:

Compound No. 1 1-(4-Chlorophenoxy)-1-(1,2,4-triazole-1-yl)-3,3-dimethyl-4-(5-trifluoromethylpyridine-2-yloxy)butan-2-one
$n_D^{20}$ 1.5383

Compound No. 2 1-(4-Phenylphenoxy)-1-(1,2,4-triazole-1-yl)-3,3-dimethyl-4-(5-trifluoromethylpyridine-2-yloxy)butan-2-one
$n_D^{20}$ 1.6191

Compound No. 3 1-[4-(5-Trifluoromethylpyridine-2-yloxy)phenoxy]-1-(1,2,4-triazole-1-yl)-3,3-dimethyl-4-(5-trifluoromethylpyridine-2-yloxy)butan-2-one
$n_D^{20}$ 1.5178

Compound No. 4 1-(4-Chlorophenoxy)-1-(1,2,4-triazole-1-yl)-3,3-dimethyl-4-(3-trifluoromethylpyridine-2-yloxy)butan-2-one
$n_D^{20}$ 1.5387

Compound No. 5 1-(4-Chlorophenoxy)-1-(1,2,4-triazole-1-yl)-3,3-dimethyl-4-(3-chloro-5-trifluoromethylpyridine-2-yloxy)butan-2-one
m.p. 136°–138° C.

Compound No. 6 1-(4-Fluorophenoxy)-1-(1,2,4-triazole-1-yl)-3,3-dimethyl-4-(3-chloro-5-trifluoromethylpyridine-2-yloxy)butan-2-one
m.p. 104°–106° C.

Compound No. 7 1-(4-Fluorophenoxy)-1-(1,2,4-triazole-1-yl)-3,3-dimethyl-4-(3-trifluoromethylpyridine-2-yloxy)butan-2-one
$n_D^{20}$ 1.5185

Compound No. 8 1-(4-Phenylphenoxy)-1-(1,2,4-triazole-1-yl)-3,3-dimethyl-4-(3-trifluoromethylpyridine-2-yloxy)butan-2-one
$n_D^{20}$ 1.5639

Compound No. 9 1-(4-Chlorophenoxy)-1-(1,2,4-triazole-1-yl)-3,3-dimethyl-4-(4-chlorophenoxy)butan-2-one
$n_D^{20}$ 1.5322

Compound No. 10 1-(4-Chlorophenoxy)-1-(1,2,4-triazole-1-yl)-3,3-dimethyl-4-(5-trifluoromethylpyridine-2-yloxy)butan-2-ol
$n_D^{20}$ 1.5010

Compound No. 11 1-(4-Fluorophenoxy)-1-(1,2,4-triazole-1-yl)-3,3-dimethyl-4-(3-chloro-5-trifluoromethylpyridine-2-yloxy)butan-2-ol
$n_D^{20}$ 1.5214

Compound No. 12 1-(4-Fluorophenoxy)-1-(1,2,4-triazole-1-yl)-3,3-dimethyl-4-(5-trifluoromethylpyridine-2-yloxy)butan-2-one
$n_D^{20}$ 1.4968

Compound No. 13 1-(4-Chlorophenoxy)-1-(1,2,4-triazole-1-yl)-3,3-dimethyl-4-(3,5-dichloropyridine-2-yloxy)butan-2-one
$n_D^{20}$ 1.5363

Compound No. 14 1-(4-Fluorophenoxy)-1-(1,2,4-triazole-1-yl)-3,3-dimethyl-4-(3,5-dichloropyridine-2-yloxy)butan-2-one
$n_D^{20}$ 1.5142

Compound No. 15 1-(4-Phenylphenoxy)-1-(1,2,4-triazole-1-yl)-3,3-dimethyl-4-(3-chloro-5-trifluoromethylpyridine-2-yloxy)butan-2-one
$n_D^{20}$ 1.6083

Compound No. 16 1-(4-Fluorophenoxy)-1-(1,2,4-triazole-1-yl)-3,3-dimethyl-4-(3-chloro-5-trifluoromethylpyridine-2-yloxy)butan-2-one hydrochloride Compound No. 17 1-(Phenoxy)-1-(1,2,4-triazole-1-yl)-3,3-dimethyl-4-(3-chloro-5-trifluoromethylpyridine-2-yloxy)butan-2-one
m.p. 80°–83° C.

Compound No. 18 1-(4-Fluorophenoxy)-1-(1,2,4-triazole-1-yl)-3,3-dimethyl-4-(2-chloro-4-trifluoromethylphenoxy)butan-2-one
m.p. 100°–102° C.

The above-listed phenoxybutyltriazole compounds possess an optically active center(s) and include 4 stereoisomers when Q is a >CH—OH group in the formula (I) and two stereoisomers when Q is a >C=O group. The compounds of the present invention do include the individual stereoisomers of these compounds, mixtures and racemates thereof.

TEST EXAMPLE 1

Cucumber (variety: Suyo) seedlings each having about two true leaves were sprayed with a solution containing 500 ppm of each of the compounds listed in Table 1 and dried by allowing to stand in a greenhouse for one day. The seedlings were inoculated with conidia of powdery mildew and allowed to stand in a greenhouse for 12 days. The severity of infection on the treated seedlings was evaluated, with the severity of infection on untreated seedlings being 100 and the absence of infection being 0. The results are shown in Table 1.

TABLE 1

| Compound No. | Severity of Infection (%) |
| --- | --- |
| 1 | 0 |
| 2 | 0 |
| 5 | 0 |
| 6 | 0 |
| 8 | 0 |
| 10 | 0 |
| 11 | 0 |
| 12 | 0 |
| 13 | 0 |
| 14 | 0 |
| 15 | 0 |
| 16 | 0 |
| 17 | 0 |
| 18 | 0 |

TEST EXAMPLE 2

Cucumber (variety: Suyo) seedlings each having about two true leaves were inoculated with conidia of powdery mildew, allowed to stand in a greenhouse for 2 days, and then sprayed with a solution containing 500 ppm of each of the compounds listed in Table 2. Twelve days after the spraying, the severity of infection on the seedlings was evaluated as in Test Example 1. The results are shown in Table 2.

TABLE 2

| Compound No. | Severity of Infection (%) |
| --- | --- |
| 1 | 0 |
| 2 | 0 |
| 5 | 0 |
| 6 | 0 |
| 8 | 0 |
| 10 | 0 |
| 11 | 0 |
| 12 | 0 |
| 14 | 0 |
| 15 | 0 |
| 16 | 0 |
| 17 | 0 |
| 18 | 0 |

TEST EXAMPLE 3

Oat (variety: Zenshin) seedlings in the two-leaf stage were sprayed with a solution containing 500 ppm of each of the compounds listed in Table 3 and dried by allowing to stand in a greenhouse for one day. Then, the seedlings were inoculated with uredospores of crown rust, and allowed to stand in a humid chamber at 20° C. for 24 hours and further in a greenhouse for 10 days. Then, the severity of infection on the seedlings was evaluated as in Test Example 1. The results are shown in Table 3.

TABLE 3

| Compound No. | Severity of Infection (%) |
| --- | --- |
| 1 | 0 |
| 2 | 4 |
| 3 | 5 |
| 4 | 8 |
| 5 | 0 |
| 6 | 0 |
| 7 | 30 |
| 8 | 0 |
| 9 | 10 |
| 10 | 0 |
| 11 | 0 |
| 12 | 0 |
| 13 | 0 |
| 14 | 0 |
| 15 | 3 |
| 16 | 0 |
| 17 | 0 |
| 18 | 0 |

TEST EXAMPLE 4

Oat (variety: Zenshin) seedlings in the two-leaf stage were inoculated with uredospores of crown rust, allowed to stand in a humid chamber at 20° C. for 2 days, and then sprayed with a solution containing 500 ppm of each of the compounds listed in Table 4. Ten days after the spraying, the severity of infection on the seedlings was evaluated as in Test Example 1. The results are shown in Table 4.

TABLE 4

| Compound No. | Severity of Infection (%) |
| --- | --- |
| 1 | 0 |
| 5 | 0 |
| 6 | 0 |
| 8 | 0 |
| 10 | 0 |
| 11 | 0 |
| 12 | 0 |
| 13 | 0 |
| 16 | 0 |
| 18 | 0 |

TEST EXAMPLE 5

Cucumber (variety: Suyo) seedlings each having about two true leaves were applied with a solution containing each of the compounds listed in Table 5 in such a manner that the solution was soil injected in an amount of active ingredient of 3 g/m$^2$, and then allowed to stand in a greenhouse for 3 days. The seedlings were inoculated with conidia of powdery mildew and allowed to stand in a greenhouse for 12 days. The severity of infection on the seedlings was evaluated as in Test Example 1. The results are shown in Table 5.

TABLE 5

| Compound No. | Severity of Infection (%) |
| --- | --- |
| 1 | 0 |
| 6 | 0 |
| 11 | 0 |
| 12 | 0 |

TEST EXAMPLE 6

Apple (variety: Starking.Delicious) seedlings each having about five true leaves were sprayed with a solution containing 500 ppm of each of the compounds listed in Table 6 and dried by allowing to stand in a greenhouse for one day. The seedlings were then inoculated with conidia of powdery mildew and allowed to stand in a greenhouse for 12 days. The severity of infection was evaluated as in Test Example 1. The results are shown in Table 6.

TABLE 6

| | Severity of Infection (%) Concentration of Active Ingredient | |
| --- | --- | --- |
| Compound | 31.3 ppm | 16.6 ppm |
| No. 6 | 0 | 0 |
| 1-(4-Chlorophenoxy)-1-(1,2,4-triazole-1-yl)-3,3-dimethylbutan-2-one (a compound described in U.S. Pat. No. 3,912,752) | 5 | 25 |

TEST EXAMPLE 7

The same procedure as in Test Example 1 was repeated except for changing the type of the compounds tested and their concentrations to evaluate the severity of infection on the seedlings. The results are shown in Table 7.

TABLE 7

| | Severity of Infection (%) Concentration of Active Ingredient | | |
| --- | --- | --- | --- |
| Compound | 15.6 ppm | 7.8 ppm | 3.9 ppm |
| No. 6 | 0 | 0 | 0 |
| 1-(4-Chlorophenoxy)-1-(1,2,4-triazole-1-yl)-3,3-dimethylbutan-2-one (a compound described in U.S. Pat. No. 3,912,752) | 0 | 5 | 10 |

The compounds of the present invention can be incorporated as an effective ingredient in agricultural and horticultural fungicides that are used widely to prevent and cure various pathogenic fungi of the groups phycomycetes, ascomycetes, basidiomycetes and fungi imperfecti. The compounds are particularly effective against pathogenic fungi that attack the part of plants above the ground level and which belong to the genus Erisiphe, Sphaerotheca, Venturia and Puccinia, such as cucumber powdery mildew, apply powdery mildew, apple scab, pear scab, wheat leaf rust and wheat smut. The compounds of the present invention also have systemic and translocative properties, so they be applied not only to the stem and foliage or seeds of plants but also to the soil in which they are absorbed by the plant roots.

The concentration and amount of the active ingredient in the fungicide prepared according to the present invention vary with the weather conditions, the type of the formulation, the timing and method of using the fungicide and, therefore, cannot be unequivocally defined, but the concentration is generally in the range of from 1 to 2,000 ppm, desirably from 25 to 500 ppm, and the amount is generally from 0.4 to 40 g, desirably from 1 to 20 g, per are (100 $m^2$). The concentration of the active ingredient in the fungicidal composition is usually 2 to 50 wt% in the case of the emulsifiable concentrate; 0.5 to 30 wt% in the case of dust; and 2 to 80 wt% in the case of wettable powder.

It is also possible to combine with other pesticides such as other fungicides, insecticides, acaricides, herbicides, plant growth regulators, etc. Sometimes synergistic effects are found. The other pesticides include organophosphorous compounds, carbamate compounds, dithio (or thiol) carbamate compounds, organic chlorine compounds, dinitro compounds, organic sulfur or organometallic compounds, antibiotics, substituted diphenyl ether compounds, urea compounds, triazine compounds, benzoylurea compounds, pyrethroid compounds, imide compounds and benzimidazole compounds, and more particularly, benzoylurea-type insecticides such as N-(2,6-difluorobenzoyl)-N'-(p-chlorophenyl)urea; pyrethroid-type insecticides such as α-cyano-3-phenoxybenzyl-2-(4-chlorophenyl)isovalerate; imide-type fungicides such as N-(3,5-dichlorophenyl)-1,2-dimethylcyclopropane-1,2-dicarboximide; benzimidazole-type fungicides such as methyl-1-(butylcarbamoyl)-2-benzimidazolecarbamate; thiocarbamate-type fungicides such as S-ethyl N-(3-dimethylaminopropyl)thiocarbamate hydrochloride; dithiocarbamate-type fungicides such as manganese ethylenebisdithiocarbamate; and urea-type fungicides such as 2-cyano-N-(ethylaminocarbonyl)-2-(methoxyimino)acetamide.

The fungicide of the present invention can be used as an aqueous dispersion or can be formulated in an emulsifiable concentrate, solution, wettable powder, granule or dust together with various agriculturally and horticulturally acceptable adjuvants such as a diluent, solvent, emulsifier and spreader.

The agricultural and horticultural fungicidal compositions are the typical compositions of the present invention.

The typical forms of the composition are the wettable powder and the emulsifiable concentrate. The typical compositions are as follows.

| | Usual | Preferable |
| --- | --- | --- |
| Agricultural and Horticultural Fungicidal Composition (concentrate): | | |
| Active ingredient | .2–80 wt % | 5–80 wt % |
| Liquid or solid carrier | (adjuvant) | 10–95 wt % |
| Surfactant | 98–20 wt % | 1–20 wt % |
| Wettable Powder: | | |
| Active ingredient | | 2–80 wt % |
| Solid carrier | | 10–90 wt % |
| Surfactant | | 3–20 wt % |
| Emulsifiable Concentrate: | | |
| Active ingredient | | 2–50 wt % |
| Liquid carrier | | 10–95 wt % |
| Surfactant | | 3–20 wt % |

Suitable adjuvants include powdery carriers such as talc, kaolin, bentonite, diatomaceous earth, silicon dioxide, clay and starch; liquid carriers such as water, xylene, toluene, dimethyl sulfoxide, dimethylformamide, acetonitrile, and alcohol; and surfactants such as sodium alkylbenzenesulfonate, polyoxyethylene alkylaryl ether, sodium naphthalenesulfonate-formaldehyde condensate, calcium ether sulfate, polyoxyethylene glycol dodecylphenyl ether, polyoxyethylene lauryl ether, polyoxyethylene fatty acid ester, sodium alkylsulfate, sulfate of polyoxyethylene alkylaryl ether, and dialkylsulfosuccinate, etc.

Some formulations of the compositions of the present invention are illustrated as follows.

| Composition No. 1: | wt. parts |
|---|---|
| Active ingredient (Compound No. 1) | 20 |
| Xylene | 60 |
| Polyoxyethylene glycol | 20 |

The components were uniformly mixed and dissolved to prepare an emulsifiable concentrate.

| | wt. parts |
|---|---|
| Composition No. 2: | |
| Active ingredient (Compound No. 5) | 5 |
| Talc | 95 |
| The components were uniformly mixed to prepare a dust. | |
| Composition No. 3: | |
| Active ingredient (Compound No. 6) | 10 |
| N—Methyl pyrrolidone | 5 |
| Xylene | 70 |
| Mixture of polyoxyethylene alkylaryl ether, polyoxyethylene alkylaryl ether polymer, polyoxyethylene fatty acid derivative and polyoxyethylene alkylaryl sulfonate | 15 |
| The components were uniformly mixed and dissolved to prepare an emulsifiable concentrate. | |
| Composition No. 4: | |
| Active ingredient (Compound No. 10) | 5 |
| Bentonite | 90 |
| Sodium ligninsulfonate | 5 |

The components were mixed with a suitable amount of water necessary for granulation and granulated to provide a granule.

| Composition No. 5: | wt. parts |
|---|---|
| Active ingredient (Compound No. 6) | 20 |
| Jeeklite | 75 |
| Sodium ligninsulfonate | 5 |

The components were uniformly mixed and pulverized to prepare a wettable powder.

While the invention has been described in detail and with reference to specific embodiments thereof, it will be apparent to one skilled in the art that various changes and modifications can be made therein without departing from the spirit and scope thereof.

What is claimed is:

1. A phenoxybutyltriazole compound represented by the following formula (III):

$$X''-\underset{}{\text{C}_6\text{H}_4}-O-\underset{\underset{N}{\overset{H}{|}}\underset{\overset{\|}{N}\diagdown N}{|}}{C}-Q-\underset{\underset{CH_3}{\overset{CH_3}{|}}}{C}-CH_2-O-\underset{N}{\text{pyridyl}}-CF_3 \quad (III)$$

with Y' substituent wherein X" is a halogen atom; Y' is a hydrogen atom or a halogen atom; and Q is a >C=O group or a >CH—OH group, or a salt thereof.

2. The compound of claim 1, wherein the compound is 1-(4-fluorophenoxy)-1-(1,2,4-triazole-1-yl)-3,3-dimethyl-4-(3-chloro-5-trifluoromethylpyridine-2-yloxy)butan-2-one, or its salt.

3. The compound of claim 1, wherein the compound is 1-(4-chlorophenoxy)-1-(1,2,4-triazole-1-yl)-3,3-dimethyl-4-(5-trifluoromethylpyridine-2-yloxy)butan-2-one, or its salt.

4. The compound of claim 1, wherein the compound is 1-(4-chlorophenoxy)-1-(1,2,4-triazole-1-yl)-3,3-dimethyl-4-(3-chloro-5-trifluoromethylpyridine-2-yloxy)butan-2-one, or its salt.

5. The compound of claim 1, wherein the compound is 1-(4-fluorophenoxy)-1-(1,2,4-triazole-1-yl)-3,3-dimethyl-4-(3-chloro-5-trifluoromethylpyridine-2-yloxy)butan-2-ol, or its salt.

6. The compound of claim 1, wherein the compound is 1-(4-fluorophenoxy)-1-(1,2,4-triazole-1-yl)-3,3-dimethyl-4-(5-trifluoromethylpyridine-2-yloxy)butan-2-one, or its salt.

7. The compound of claim 1, wherein the compound is 1-(4-chlorophenoxy)-1-(1,2,4-triazole-1-yl)-3,3-dimethyl-4-(5-trifluoromethylpyridine-2-yloxy)butan-2-ol, or its salt.

8. An agricultural fungicidal composition which comprises a phenoxybutyltriazole compound or a salt thereof as an active ingredient and an agriculturally and horticulturally acceptable adjuvant, said phenoxybutyltriazole compound being represented by the following formula (III):

$$X''-\underset{}{\text{C}_6\text{H}_4}-O-\underset{\underset{N}{\overset{H}{|}}\underset{\overset{\|}{N}\diagdown N}{|}}{C}-Q-\underset{\underset{CH_3}{\overset{CH_3}{|}}}{C}-CH_2-O-\underset{N}{\text{pyridyl}}-CF_3 \quad (III)$$

with Y' substituent wherein X" is a halogen atom; Y' is a hydrogen atom or a halogen atom; and Q is a >C=O group or a >CH—OH group, or a salt thereof.

9. The composition of claim 8, wherein the compound is 1-(4-fluorophenoxy)-1-(1,2,4-triazole-1-yl)-3,3-dimethyl-4-(3-chloro-5-trifluoromethylpyridine-2-yloxy)butan-2-one, or its salt.

10. The composition of claim 8, wherein the compound is 1-(4-chlorophenoxy)-1-(1,2,4-triazole-1-yl)-3,3-dimethyl-4-(5-trifluoromethylpyridine-2-yloxy)butan-2-one, or its salt.

11. The composition of claim 8, wherein the compound is 1-(4-chlorophenoxy)-1-(1,2,4-triazole-1-yl)-3,3-dimethyl-4-(3-chloro-5-trifluoromethylpyridine-2-yloxy)butan-2-one, or its salt.

12. The composition of claim 8, wherein the compound is 1-(4-fluorophenoxy)-1-(1,2,4-triazole-1-yl)-3,3-dimethyl-4-(3-chloro-5-trifluoromethylpyridine-2-yloxy)butan-2-ol, or its salt.

13. The composition of claim 8, wherein the compound is 1-(4-fluorophenoxy)-1-(1,2,4-triazole-1-yl)-3,3-dimethyl-4-(5-trifluoromethylpyridine-2-yloxy)butan-2-one, or its salt.

14. The composition of claim 8, wherein the compound is 1-(4-chlorophenoxy)-1-(1,2,4-triazole-1-yl)-3,3-dimethyl-4-(5-trifluoromethylpyridine-2-yloxy)butan-2-ol, or its salt.

* * * * *